United States Patent [19]  [11] 3,973,031
Molle et al.  [45] Aug. 3, 1976

[54] GULONIC ACID SALT
[75] Inventors: Jean Louis Molle, Villeurbanne-St. Georges; Jean Christian Boch, Neris-les-Bains, both of France
[73] Assignee: A.E.C. Societe de Chimie Organique et Biologique, Paris, France
[22] Filed: Jan. 27, 1975
[21] Appl. No.: 544,572

Related U.S. Application Data
[62] Division of Ser. No. 396,803, Sept. 13, 1973, Pat. No. 3,910,960.

[30] Foreign Application Priority Data
Sept. 15, 1972 France .............................. 72.32896

[52] U.S. Cl. ............................................... 424/278
[51] Int. Cl.² ....................................... A61K 31/335
[58] Field of Search .................................. 424/278

[56] References Cited
UNITED STATES PATENTS
3,915,993  10/1975  Tanoura et al. .................... 424/278

Primary Examiner—Donald B. Moyer
Attorney, Agent, or Firm—Stevens, Davis, Miller & Mosher

[57] ABSTRACT
Calcium diacetone-2-ketogulonate, which is a new therapeutically useful compound.

4 Claims, No Drawings

GULONIC ACID SALT

This is a division, of application Ser. No. 396,803, filed 9/13/73 now U.S. Pat. No. 3,910,960.

The present invention relates to a salt of diacetone-2-ketogulonic acid having valuable pharmacological properties.

Diacetone-2-ketogulonic acid (DKG) has the formula:

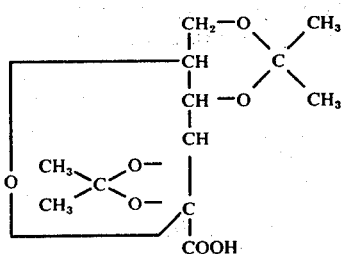

It is a product known to be an intermediate for vitamin C. Its preparation is described by Velluz (Substances naturelles de synthese, Masson, 1951, Vol. I, page 8 and thereafter). DKG is an unstable compound which decomposes easily in the presence of mineral acids and cannot withstand heating or pressure. It cannot be stored in aqueous solution, even in the presence of a stabiliser such as tris(hydroxymethyl)aminomethane (TRIS). Under pressure, the acid undergoes considerable degradation. Consequently, it is impossible to use DKG on therapy.

The preparation of potassium diacetone-2-ketogulonate has been described in J. Agric. Chem. Soc. Japan, 1951-52, 25, 198-20, but the use of this compound in therapy is not described.

It has now been surprisingly found that the calcium salt of DKG possesses noteworthy stability, especially stability on storage and stability under pressure, and can be used effectively as a therapeutic agent because of its valuable properties particularly its hypocholesteremia-inducing and hypolipemia-inducing properties and its property of reducing fatigue.

The invention thus provides diacetone-2-ketogulonic acid calcium salt. The salt can be prepared by reacting DKG with a calcium-containing base (e.g. calcium carbonate or hydroxide).

The present invention also provides pharmaceutical compositions which comprise, as active ingredient, the DKG calcium salt in association with a pharmaceutically acceptable carrier or coating. The compound is suitably administered orally.

Solid compositions for oral administration include compressed tablets, dragees, pills, powders, granules and effervescent powder in sachets. In such solid compositions, the active compound is admixed with at least one inert diluent such as starch, sucrose or lactose. The compositions may also comprise, as is normal practice, additional substances other than inert diluents, e.g. lubricating agents such as magnesium stearate. For making the tablets, conventional compression adjuvants, such as Avicel (crystalline cellulose from the American Viscose Corporation) and Precirol (a mixture of glyceryl mono-, di- and tri-stearates and palmitates from Messrs. Gattefosse), are generally used.

Liquid compositions for oral administration include pharmaceutically acceptable emulsions, solutions, suspensions, syrups and elixirs containing inert diluents commonly used in the art such as water and liquid paraffin. Besides inert diluents such compositions may comprise adjuvants, such as wetting and suspending agents, and sweetening, flavouring, perfuming and preserving agents. The compositions according to the invention for oral administration, also include capsules of absorbable material such as gelatin, containing the active substance with or without the addition of diluents or excipients.

The percentage of active ingredient in the compositions of the invention may be varied, it being necessary that it should constitute a proportion such that a suitable dosage shall be obtained. Obviously, several unit dosage forms may be administered at about the same time. The dose employed depends upon the desired therapeutic effect, the route of administration and the duration of the treatment. Each unit dose form generally contains between 0.1 and 2g. of active compound.

The compositions can also contain a stabiliser, such as TRIS, for example in an amount of 1 to 5%, especially about 2%, by weight of the active compound.

The tablets produced possess noteworthy stability which can be further improved by the presence of auxiliary stabilisers, as indicated above.

The composition can be administered at a dose of 0.250 g. to several grams (for example, 3 to 4 g.) of the active ingredient per day.

The invention is illustrated by the following Example.

EXAMPLE 1

2.1 Kg. of calcium carbonate (or an equivalent amount of calcium hydroxide) and 18 liters of water in a 30 liter reactor were heated with 7 kg. of DKG added in small portions with vigorous stirring over about 3 hours. A large amount of foaming occurred. The mixture was then left to stand for at least one hour at ambient temperature whilst being stirred vigorously. The excess calcium carbonate was filtered off and washed with 1 liter of water. The calcium salt was obtained either by evaporation of the solution in vacuo or by precipitation with alcohol/ether to give calcium diacetone-2-ketogulonate (CeDKG) of formula:

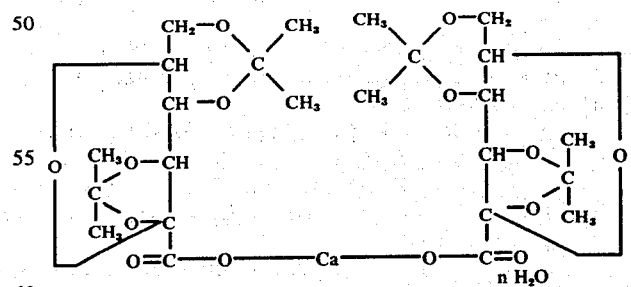

in a yield of about 85% by weight.

Ca DKG $[(C_{12}H_{17}O_7)_2Ca.nH_2O]$ is a light, fine, white powder which has practically no smell but does have a bitter taste; it is very soluble in water, soluble in alcohol, sparingly soluble in chloroform and practically insoluble in ether.

pH = 6–7 (as a 0.1M aqueous solution) $\alpha_D^{20} = -11.3°$

Ca% = 6.08–6.01 (by direct complexometry in the presence of murexide).

The amount of CaDKG can be determined by chelation with copper ions, followed by complexometry after extraction of the chelate formed; the product contained at least 96% by weight of CaDKG.

In thin layer chromatography on silica (Merck HF 254+366) with butanol/acetic acid/water (4/1/1) as solvent, a single spot with an Rf value of about 0.7 was found. The spot was visible in ultra-violet light at 254 m$\mu$ and can be developed by treatment with phosphomolybdic acid and permanganate in sulphuric acid.

This salt possesses good stability; when heated for more than 100 days at 60°C., it does not show any trace of degradation. This stability can be further improved by adding small amounts (e.g. about 2% by weight) of TRIS.

The TRIS can be added to the aqueous solution after removing the calcium carbonate. This Example was thus carried out again but adding 105 g. of TRIS to the solution at this stage.

Ca DKG alone or containing about 2% of TRIS can be tabletted in the presence of the usual compression adjuvants such as Avicel and Precirol; the tablets so obtained can be converted into dragees in known manner.

The results of toxicological, pharmacological and clinical tests carried out on Ca DKG are now given.

(A) - Toxicity

The acute toxicity of Ca DKG when administered intravenously and orally to mice (Swiss SPF) was investigated. The $LD_{50}$ of the compound when administered intravenously is 1.375 g./kg. in the male and 1.275 g./kg. in the female. When administered orally it is greater than 8 g./kg. in both males and females. The $LD_{50}$ of the compound when administered orally to male and female rats (SPF) was greater than 8 g./kg.

The long-term toxicity of Ca DKG was investigated in male or female rats over three months. The growth of the animals was not effected even at doses of 1,600 mg./kg.

Histological examination of the digestive organs, kidneys, spleen, thyroid and adrenal glands, gonads, heart and encephalon did not reveal any lesions which could indicate intolerance of the animals to the product.

The tolerance of the product was investigated in rats and dogs.

Ca DKG, at the doses of 100, 500 or 1,500 mg./kg. administered to rats, did not cause any changes in the animal's growth.

From the haematological point of view, the product did not adversely affect the erythrocytes or leukocytes.

The weights of the organs of the treated animals do not differ statistically from the weights of the organs of the control animals.

In dogs, doses of 1 g./day did not affect the appetite of the animals. No intolerance was noted. In particular, no sign of diarrhoea or vomiting or skin symptoms was noticed.

The various blood and urine determinations carried out on these animals remained normal. A fall in the serum cholesterol is noted; this fall occurred after 15 days of treatment and under an identical diet.

Overall Ca DKG has proved to be a product of low toxicity in various animal species tested.

(B) - Pharmacological Investigation

The pharmacological investigation of Ca DKG demonstrated its effect on hypercholesteremia and hyperlipemia.

a. The effect of Ca DKG on the proportion of cholesterol in the serum of normal rats was investigated.

The rats, subjected to an exclusively fluid diet, were given, after 6 hours, Ca DKG at a dose of 1 g./kg. administered orally. 18 Hours later, 5 to 6 ml. of blood were removed and cholesterol determinations were carried out. The product, after a single administration, did not alter the proportion of cholsterol in the serum as compared to the control animals.

| | Total cholesterol mg./100 ml. |
|---|---|
| Control animals | 80 ± 10 |
| Treated animals | 77.5 ± 10 | b. The effect on hypercholesteremia in rats subjected to an injection of Triton WR 1339 (a surface active agent from Rohm and Haas) was investigated. A great increase in total cholesterol can be caused by the intravenous injection of 300 mg./kg. of Triton WR 1339 (J. Exptl. Med., 1953, 97, 117). The results of the determinations carried out 18 hours after the injection of Triton WR 1339, firstly on control animals and secondly on animals treated with 1 g./kg. of Ca DKG at the time of the Triton injection and 2 hours before the samples were removed, showed that the product had a noteworthy hypocholesteremic-inducing effect:

| | Total Cholesterol g./liter |
|---|---|
| Control animals (which received Triton only) | 2.40 ± 0.32 |
| Treated animals | 1.41 ± 0.38 |

Ca DKG, administered twice at a dose of 1 g./kg. on the first occasion at the same time as the Triton and on the second occasion 16 hours later, caused a large drop in cholesteremia which could be as much as 40%.

During another experiment, Ca DKG was given in a single dose of 1g./kg. at the time of the Triton injection. The results confirmed the preceding experiment:

| | Total Cholesterol g/liter |
|---|---|
| Controls which received Triton | 2.41 ± 0.23 |
| Treated animals | 1.68 ± 0.24 |

The reduction in the cholesteremia was about 30%.

c. The effect on the drop in total lipids was investigated under the same conditions. The determination of the lipids was carried out by the Delsal method (Fleury, Technical Notes in Biological Chemistry).

| | Total lipids in the serum, g/l. |
|---|---|
| Controls which did not receive Triton | 4.28 ± 0.30 |
| Controls which received Triton | 15.32 ± 0.86 |
| Treated animals | 12.42 ± 1.31 |

When administered once at a dose of 1 g./kg. at the time of the Triton injection, Ca DKG reduced the proportion of lipids in the serum by 18%. The glycemia of animals which received 1 to 2 g./kg. of Ca DKG was not changed.

d. The effect of Ca DKG on hypercholesteremia and hyperlipemia in rabbits caused by a cholesterol-rich diet was investigated.

Male rabbits of average weight 2 kg. were fed a diet based on a subsistence foodstuff provided by Messrs. U.A.R., [7, rue Marechal Gallieni, 91 Villemoisson sur Orge, France (Usine d'Alimentation Rationnelle)], and called "Complete Subsistence Foodstuff for the Care of Rabbits" (U.A.R. Technical Note No. 112); as much drinking water as desired was available. The animals were divided into batches of 5 and were also given the following ingredients administered orally, by means of a syringe, over 21 days.

Batch No. 1 — Water
Batch No. 2 — Ca DKG, 500 m./kg.
Batch No. 3 — Cholesterol 250 mg./kg. (10% solution in olive oil)
Batch No. 4 — Cholesterol 250 mg./kg. (10% solution in olive oil) + Ca DKG 500 mg./kg. administered orally.

On days 0, 7, 14 and 21, blood was removed from the marginal vein of the ear of each animal and the following measurements were carried out on the serum: Determination of blood cholesterol Determination of total blood lipids. The following Table gives the results in the form of averages for each batch:

| Days | Cholesterol in g/liter | | | |
|---|---|---|---|---|
| | 0 | 7 | 14 | 21 |
| Batch No. 1 | 0.52 | 0.55 | 0.61 | 0.57 |
| Batch No. 2 | 0.62 | 0.47 | 0.56 | 0.42 |
| Batch No. 3 | 0.44 | 0.84 | 0.94 | 1.18 |
| Batch No. 4 | 0.45 | 0.82 | 0.64 | 0.75 |
| | Total Lipids in g/liter | | | |
| Batch No. 1 | 3.90 | 3.51 | 3.07 | 3.34 |
| Batch No. 2 | 3.34 | 3.05 | 3.51 | 2.93 |
| Batch No. 3 | 3.84 | 4.20 | 4.49 | 4.58 |
| Batch No. 4 | 3.35 | 4.44 | 3.38 | 3.48 |

It can be seen that Ca DKG limits the rise in cholesteremia and lipemia in the animals which are given a cholesterol-rich diet. Moreover, in the animals on a normal diet, it slightly decreases the cholesterol or lipid levels or keeps them in the vicinity of the normal values. During another experiment, 2 kg. male rabbits were given cholesterol by oral administration (250 mg./kg. as a 10% solution in olive oil).

They were divided into batches of 5:
Batch No. 1 — Cholesterol 250 mg./kg. for 55 days
Batch No. 2 — Cholesterol 250 mg./kg. for 28 days, followed by water,
Batch No. 3 — Cholesterol 250 mg./kg. for 28 days, followed by Ca DKG 500 mg./kg.

The determination of blood cholesterol and total blood lipids were carried out on days 28, 34, 41 and 55. The results are as follows:

| Days | Cholesterol in g/litre | | | | |
|---|---|---|---|---|---|
| | 28 | 34 | 41 | 48 | 55 |
| Batch No. 1 | 1.35 | 1.75 | 2.08 | 2.40 | 2.50 |
| Batch No. 2 | 1.46 | 1.01 | 0.65 | 0.55 | 0.58 |
| Batch No. 3 | 1.46 | 0.65 | 0.55 | 0.55 | 0.57 |
| | Total Lipids in g/litre | | | | |
| Batch No. 1 | 4.82 | 5.15 | 6.10 | 7.60 | 9.00 |
| Batch No. 2 | 4.95 | 4.60 | 3.32 | 3.55 | 3.30 |

-continued

| Days | Cholesterol in g/litre | | | | |
|---|---|---|---|---|---|
| | 28 | 34 | 41 | 48 | 55 |
| Batch No. 3 | 4.45 | 3.63 | 3.70 | 3.55 | 3.70 |

It can be seen that Ca DKG reduces the proportions of cholesterol and total lipids to normal more rapidly than is the case when the cholesterol-rich diet is simply stopped.

On killing the animals, it was found that the accumulation of fat in the liver, manifesting itself in fatty infiltrations of the hepatic parenchyma, is reduced by the product.

Furthermore, Ca DKG inhibited the appearance of atheromas or greatly reduced the atheromatic plaques of the aorta caused by the accumulation of cholesterol to such a point that no extensive confluent infiltrations were found on the aortas of the treated animals.

e. Ca DKG does not appear to have any potentiating or inhibiting effect on anti-coagulants (Tromexan, pindione).

f. The product does not inhibit or excite the central nervous system as experiments based on conditioned reflexes have demonstrated.

On the other hand, in fatigue tests carried out by means of the swimming test in mice, an increase in the swimming time is observed under the influence of the product.

Experiments on rats in a revolving cage were carried out; Ca DKG appears to act on muscular fatigue. Its effect on the motility of rats can probably be explained by a peripheral muscular point of impact, which would tend to improve the performance and to delay or decrease fatigue.

g. The product, administered orally, does not change the arterial pressure nor the respiration of dogs treated with chloralose or of rabbits treated with urethane. The reactivity to adrenaline, noradrenaline, isopropylnoradrenaline and acetylcholine remained unchanged after either gastric or duodenal administration of Ca DKG.

h. An attempt was made to find out whether Ca DKG behaved as a precursor of ascorbic acid.

Guinea pigs were subjected to a diet deficient in vitamin C and certain animals were given, at the same time as the deficient diet, either vitamin C or Ca DKG at a dose of 75 mg/kg/day, administered orally.

The treatment was continued for 20 days. After this time, in the batch not fed with vitamin C. eight animals out of twelve had died. In the batch receiving vitamin C, there were no deaths. In the batch receiving Ca DKG, there were nine deaths out of twelve.

It is thus seen that the high death rate resulting from the deficient diet is eliminated by vitamin C but not by Ca DKG.

Determination of ascorbic acid in the adrenal glands gave the following results:

| | |
|---|---|
| Deficient diet | 14 µg/100 mg. |
| Deficient diet + Vitamin C | 71 µg/100 mg. |
| Deficient diet + Ca DKG | 18 µg/100 mg. |

It is thus proved that Ca DKG cannot be a precursor in the synthesis of vitamin C.

In conclusion, Ca DKG, a product of low acute or chronic toxicity, possesses noteworthy hypocholesteremia and hypolipemia-inducing effects. Furthermore, it possesses an anti-fatigue effect, the point of impact of which appears to be muscular.

C — - Clinical Investigation

Doses of 0.5 g. of Ca DKG per unit (dragee or tablet) were administered to patients suffering from hypercholesteremia, hyperlipemia or hypertriglyceremia. The doses varied between 2 and 6 doses per day.

Determinations of cholesterol, total lipids and triglycerides showed that the product caused a large drop (cholesterol 23%, total lipids 32% triglycerides 29%).

Out of 100 clinical cases investigated, 75 good and very good results, 15 average results and 10 poor or zero results were obtained.

Ca DKG has, furthermore, been administered to asthenic patients who have benefited to a large extent from the anti-fatigue effect of the product.

Some clinical cases are given below to illustrate the effect of Ca DKG on the cholesterol, lipid and triglyceride levels.

Case No. 1. Male - 42 years

This patient was one in whom hereditary diabetes was diagnosed four years ago; the diabetes manifests itself biologically by a glycemia rise of from 1.60 to 3.10 over one hour during induced hyperglycemia. For four years the patient had taken two tablets per day of a long-acting glucophage.

The cholesterol level was 2.70, the lipid level was 8.25 and the triglyceride level was 4.05.

He was given 6 dragees per day of Ca DKG for two months. Two months later, the cholesterol level was 2.45, the lipid level was 6.50 and the triglyceride level was 1.30.

Since an identical diet was followed during this period of treatment, the product clearly has a high activity particularly on the triglyceride level.

Case No. 2. Female - Age 72

A recently detected diabetic with glycemia at 2.90. The diabetes is treated by diet and by administration of half a glibenclamide tablet per day and, after one month, the cholesterol level was 3.25.

At this time, 6 dragees per day of Ca DKG were added and, one month later, the cholesterol level was 2.75.

The patient felt physiologically well and can tolerate perfectly the double treatment which will be continued.

Case No. 3. Female - 54 years

A minor diabetic with glycemia at 1.28 when resting and when fasting; she has not followed a diet nor undergone treatment. Her hypoglycemia showed a peak at 2.14 whilst the cholesterol level rose to 3.90.

A long-acting oral treatment with biguanidines was prescribed and two dragees of Ca DKG were also given, morning and evening. The cholesterol level after six weeks was 2.65, i.e. a 32% fall.

The clinical and biological benefit is thus clear.

Case No. 4. Female - 57 years

A diabetic patient who had suffered from diabetes for five to six years. The total lipid level was 9 g. even with a diabetic diet strictly adhered to.

She was given 6 dragees per day of Ca DKG; after one month, the lipid level was 4.50.

The improvement in her lipid level and a feeling of better health was not accompanied by a parallel change in her diabetes.

Case No. 5. Female - 57 years

A patient worried by a family history of myocardial infarction. The cholesterol level was 3.80.

She was given 4 dragees per day of Ca DKG for three months. The cholesterol level was 3.05 after six weeks and 2.95 after three months of treatment. A fall of 22% was thus observed.

Case No. 6. Female - 62 years

Relatively obese patient. Cholesterol level high at 3.60. No diabetes. No functional symptoms except for a certain lassitude.

Six dragees of Ca DKG per day were given for six weeks but no change in diet was made. The cholesterol level was 2.80; this was a significant decrease which was accompanied by an improvement in the general well being of the person.

Case No. 7. Male - 67 years

He came for a consultation through fear of hypertension following headaches and vertigo. Glycemia of the diabetic type (2.80); cholesterol level was at 5.80 and total lipid level was 28 g. with very milky serum.

6 Tablets per day of Ca DKG were administered and, after 1 month, the cholesterol level was 2.20 and the lipid level was 6 g.

The treatment was interrupted by the person concerned and, two months later, his cholesterol level was 3.10 and his total lipid level was 26 g.; the serum being again milky.

A second course of treatment of 6 dragees of Ca DKG per day brought the cholesterol level back to 1.90 and the lipid level to 6 g.

The satisfactory effect of the product was demonstrated particularly by the experiment following the stopping of the treatment.

An improvement in the general condition of this patient and a decrease in vertigo was observed.

Case No. 8. Male - 40 years

He was in hospital for vertigo and nausea as well as unstable and usually high arterial pressure. The total lipid level was situated at 9.8, with a Burnstein reaction at 129 U.

Since the clinical and biological investigation did not reveal other symptoms, he was given six dragees per day of Ca DKG for six weeks. The vertigo and nausea disappeared and the total lipid level was 7.2, and the Burnstein reaction was 92 U. The biological and clinical effect of Ca DKG appears to be favourable with this patient.

Case No. 9. Male - 53 years

A diabetic treated with hypoglycemia-inducing sulphamides. High hyperlipemia was found.

The cholesterol level was 3.74, the total lipid level was 17.50 and the triglyceride level was 9.60.

He was given 6 dragees per day of Ca DKG for six weeks. The cholesterol level was 3.20, the total lipid level was 7.75 and triglyceride level was 2.90.

The results were good since the cholesterol level had fallen by 14.4%, the total lipid level by 55.7% and the triglyceride level by 69.8%.

Case No. 10. Female - 26 years

A patient with discrete hypothyroidism treated previously with thyroglobulin. The treatment had been stopped for two months and only a low calorie diet had then been followed.

The cholesterol level was 3.80, the total lipid level was 7.85 and the triglyceride level was 2.60.

She was given 6 dragees of Ca DKG per day for three weeks, after which the cholesterol level was 2.55, the total lipid level was 6g. and the triglyceride level was 1.10. The results are good.

Case No. 11. Female - 55 years

Bad evolutional myopia with retinal degeneration in an obese person who had been in this condition for 15 years.

Previous treatments: vascular protecting agents (rutin, nicotinamide) and anthacyanoside vitamin E with mediocre results.

The cholesterol level was 3.20, total lipid level was 11.30 and the triglyceride level was 5.

She was given 6 tablets per day of Ca DKG for 4 months.

A decrease in the exuding condition of the areas of peripheral degeneration in the retina was observed. The cholesterol level was 1.90; the total lipid level was 7.10 and the triglyceride level was 1.70.

The patient lost 12 kgs. and felt much better.

The tolerance of Ca DKG was good. The product proved to be effective.

Case No. 12. Female - 62 years

Atherosclerotic hypertensive patient having retinopathy with appearance of a few small exudates. Headaches and floating spots before the eyes. Previous treatments: various hypotensive agents, followed irregularly. The cholesterol level was 3.90, the total lipid level was 6.30 and the triglyceride level was 0.90.

Four dragees of Ca DKG per day were given for eight months, the functional symptoms and the exudates both disappeared.

The cholesterol level was 2.30, the total lipid level was 5.85 and the triglyceride level was 0.87.

The effectiveness of the product was thus good with respect to the functional symptoms, the exudates and the cholesterol.

Case No. 13. Male - 42 years

Xanthelasma of the upper and lower lids of the left eye had recently appeared (a few months previously). No previous treatment. The cholesterol level was 3.95, the total lipid level was 8 g. and the triglyceride level was 1.95.

Six tablets of Ca DKG per day were given for six weeks, followed by four tablets per day for four and a half months.

The cholesterol level was 2.30, the total lipid level was 7.20 and the triglyceride level was 0.96.

The effectiveness of Ca DKG was again demonstrated.

Case No. 14. Male - 54 years

Pathological cataract with complications. Secondary macular degeneration of the right eye.

The patient was slightly plethoric with a prediabetic condition.

The cholesterol level was 2.60, the total lipid level was 12.20 and the triglyceride level was 5.

Six tablets of Ca DKG per day were given for 60 days, followed by four tablets per day for 60 days; finally six tablets per day for 13 months.

The cholesterol level fell to 2.25, the total lipid level to 7.5 and the triglyceride level to 1.35. The tolerance of the product and its effectiveness were good.

By way of summary, the use of Ca DKG gave satisfactory treatment of lipid excess, whether they be total lipids, cholesterol or triglycerides.

The compositions exhibit, in addition to therapeutic activity, a remarkable tolerance both general and digestive.

Examples of the pharmaceutical compositions of the invention are given below.

EXAMPLE 2

| Dragees | | |
|---|---|---|
| Ca DKG (expressed as the anhydrous salt) | 0.500 | g. |
| Excipient for the core: microcrystalline α-cellulose, glyceryl stearate, magnesium stearate, in a quantity sufficient to make up to | 0.61 | g. |
| Excipient for the coating: Talc, gelatin, gum arabic, white sugar, purified water, titanium oxide, white wax, spermaceti, rectified ether, denatured industrial alcohol, tartrazine, a new coccine in a quantity sufficient to make up to | 1.1 | g. |
| Tablets | | |
| Ca DKG (expressed as the anhydrous salt) | 0.500 | g. |
| Sodium Saccharin | 0.037 | g. |
| Raspberry flavouring | 0.01 | g. |
| Sugar | 2 | g. |
| Magnesium Stearate | 0.015 | g. |
| Effervescent Double Sachet I | | |
| Alkaline Sachet B | | |
| Ca DKG | 0.564 | g. |
| Glycine sodium carbonate | 2 | g. |
| Sugar | 3 | g. |
| Acid Sachet A | | |
| Citric Acid | 1.5 | g. |
| Sodium Saccharin | 0.001 | g. |
| Raspberry Flavouring | 0.15 | g. |
| Sugar | 3 | g. |
| Effervescent Double Sachet II | | |
| Alkaline Sachet B | | |
| Ca DKG | 1.15 | g. |
| Sodium bicarbonate | 1.5 | g. |
| Sorbitol | 0.35 | g. |
| Acid Sachet A | | |
| Acetic acid | 1.8 | g. |
| Sodium saccharin | 0.005 | g. |
| Mandarin orange flavouring | 0.055 | g. |
| Lemon flavouring | 0.020 | g. |
| Sorbitol | 1.12 | g. |

We claim:

1. A pharmaceutical composition comprising, as active ingredient, calcium diacetone-2-ketogulonate in association with a pharmaceutically acceptable carrier or coating.

2. A pharmaceutical composition according to claim 1 in unit dosage form for oral administration which comprises calcium diacetone-2-ketogulonate in association with a pharmaceutically acceptable carrier or coating, the amount of said salt in the composition being between 0.1 and 2 g.

3. Method for the treatment of hypercholesteremia or hyperlipemia in a patient, which comprises administering to the patient an effective amount of calcium diacetone-2-ketogulonate.

4. Method according to claim 3 in which 0.250 g to 4.0 g. of calcium diacetone-2-ketogulonate are administered to the patient or person daily.

* * * * *